(12) United States Patent
Inagaki et al.

(10) Patent No.: US 6,704,441 B1
(45) Date of Patent: Mar. 9, 2004

(54) INSPECTION SYSTEM

(75) Inventors: Daisuke Inagaki, Osaka (JP); Yasuhisa Ikushima, Osaka (JP)

(73) Assignee: Keyence Corporation, Osaka (JP)

( * ) Notice: Subject to any disclaimer, the term of this patent is extended or adjusted under 35 U.S.C. 154(b) by 0 days.

(21) Appl. No.: 09/366,555

(22) Filed: Aug. 4, 1999

(30) Foreign Application Priority Data

Feb. 4, 1999 (JP) ............................................ 11-027919

(51) Int. Cl.[7] .................................................. G06K 9/00
(52) U.S. Cl. ........................ 382/145; 382/173; 382/305; 717/100; 714/763; 209/545
(58) Field of Search ................................ 382/145, 142, 382/173, 141, 305; 328/56, 57, 58; 209/524, 545; 250/223 B; 198/340, 408, 576; 717/100; 702/81, 83, 134, 113; 714/763

(56) References Cited

U.S. PATENT DOCUMENTS

| | | | | |
|---|---|---|---|---|
| 4,385,699 A | * | 5/1983 | Ashina | 209/538 |
| 4,414,566 A | * | 11/1983 | Peyton et al. | 382/142 |
| 4,519,041 A | * | 5/1985 | Fant et al. | 382/141 |
| 4,884,696 A | * | 12/1989 | Peleg | 209/576 |
| 4,924,107 A | * | 5/1990 | Tucker | 250/559.46 |
| 5,095,204 A | * | 3/1992 | Novini | 250/223 B |
| 5,305,391 A | * | 4/1994 | Gomibuchi | 382/142 |
| 5,345,515 A | * | 9/1994 | Nishi et al. | 382/111 |
| 5,602,890 A | * | 2/1997 | Gray et al. | 378/57 |
| 6,226,081 B1 | * | 5/2001 | Fantone et al. | 356/427 |
| 6,408,429 B1 | * | 6/2002 | Marrion, Jr. et al. | 717/100 |

FOREIGN PATENT DOCUMENTS

| | | |
|---|---|---|
| EP | 0 159 364 A1 | 10/1985 |
| GB | 2 238 151 A | 5/1991 |
| JP | 08-153941 * | 6/1996 |
| WO | WO 98/22909 | 5/1998 |

* cited by examiner

Primary Examiner—Jayanti K. Patel
Assistant Examiner—Sheela Chawan
(74) Attorney, Agent, or Firm—Morgan, Lewis & Bockius LLP

(57) ABSTRACT

An inspection system in which an inspection of a work is conducted by processing image data of the work. The inspection system includes a data processor for storing image data of the work in a memory and executing data processing of the image data stored in the memory, a set process storing section for dividing a plurality of inspection items, which need different data processing respectively, of the image data stored in the memory into a plurality of groups within performance of the data processor and storing the plurality of inspection items, and an execution controller for causing the data processor to execute sequentially data processing of the image data stored in the memory in unit of group which is stored in the set process storing section.

8 Claims, 5 Drawing Sheets

| SETTING 1 | SETTING 2 | | SETTING 6 |
|---|---|---|---|
| OUTER DIAMETER, INNER DIAMETER, AREA | SURFACE DEFECT, ANGLE, WIDTH DIMENSION, AREA | | |

INSPECTION SYSTEM

BACKGROUND OF THE INVENTION

1. Field of the Invention

The present invention relates to an inspection system for conducting various inspections of an inspection object by processing image data which are collected by picking up an image of the inspection object using an imaging device.

2. Description of the Related Art

It has already been common to employ an inspection system which can conduct various inspections of an inspection object (referred to as a "work" hereinafter), e.g., various decisions concerning quality of shape, accuracy of dimension, presence of surface defect, quality of coating/printing, and the like, by extracting feature quantities after an image of a product which is carried on a production line is picked up as the work by using an imaging device and then image data which are so collected are processed. According to such inspection system, when the feature quantities are extracted by processing the image data, they are detected by executing data processing, which corresponds to type of inspection, so as to satisfy inspection contents. For instance, as with the image detected by picking up an end surface of the circular cylinder work, the process for deciding the "accuracy of dimension" detects maximum/minimum values of the dimension on a main scanning line of the imaging device in an area occupied by the image of the work, and also the process for deciding the "surface defect" decides whether or not either a shade of the image or difference in color exceeds a predetermined threshold value. Therefore, it is impossible to execute these processes simultaneously by a single central processing unit (CPU).

In this manner, processes for extracting different feature quantities according to the type of inspection are carried out in the conventional inspection system. Thus, normally the processing system is equipped with a parallel processing circuit so as to execute such processes. However, since a large scale circuit and a large scale memory are needed to carry out a variety of processes simultaneously, the problems of a rise in the cost, an increase in size of the system, and the like are caused. For this reason, in the case that plural types of inspections which need different feature quantities as above are carried out by the conventional inspection system, several types of inspection which can be executed simultaneously are conducted and then other types of inspection are conducted by picking up the image of the work once again.

Therefore, in the conventional inspection system, the image of the work must be picked up again and again every time when different types of inspection are conducted, whereby the time required for the inspection is prolonged because of such process and also the work must stand still during such time. As a result, there has been the problem that a mechanism for keeping the work in the still condition must be provided to the production line.

On the other hand, in order to make the inspection system conduct plural types of inspection simultaneously based on the image being picked up at a time, a plurality of processors or processing circuits which correspond to respective inspections must be provided. As a result, there have been the problems that the cost of the inspection system per se is raised, performance of the inspection system becomes excessive if only few types of inspection are conducted, and a size of the inspection system is increased.

SUMMARY OF THE INVENTION

The present invention has been made in view of the above circumstances, and it is an object of the present invention to provide an inspection system capable of conducting a variety of different inspections by picking up an image of a work only once.

In order to achieve the above object, according to the present invention, there is provided an inspection system for conducting inspections of an inspection object by processing image data which are collected by picking up an image of the inspection object, comprising: image data storing means for storing the image data of the inspection object; data processing means for executing data processing of the image data stored in the image data storing means; inspection item storing means for dividing a plurality of inspection items, which need different data processing respectively, of the image data into a plurality of groups within predetermined conditions and storing the plurality of inspection items; and executing means for causing the data processing means to execute sequentially data processing of the image data stored in the image data storing means in unit of group so as to correspond to the plurality of inspection items stored in the inspection item storing means.

According to the inspection system of the present invention, first the image of the inspection object is picked up only once, and then the data processing of the image data is executed sequentially in unit of group to correspond to the inspection items which are contained respectively in the plurality of groups being stored previously.

DETAILED DESCRIPTION OF THE PREFERRED EMBODIMENT

An embodiment of the present invention will be described in detail with reference to the accompanying drawings hereinafter.

Figure 1:
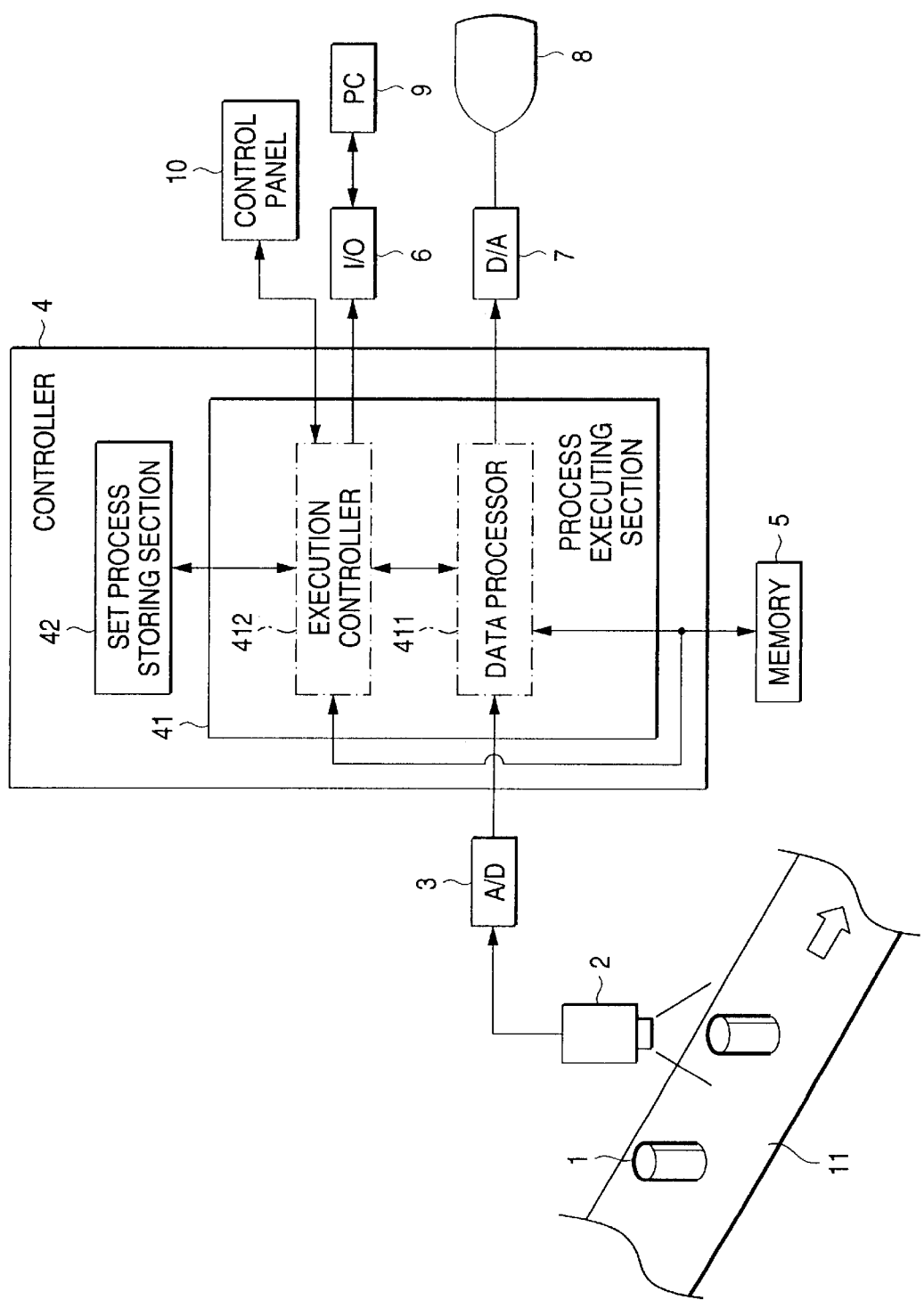
FIG. 1 is a block diagram showing an example of a configuration of an inspection system according to the present invention.

FIG. 1 is a block diagram showing an example of a configuration of an inspection system according to the present invention.

An inspection object (referred to as a "work" hereinafter) is carried successively by a belt conveyor 11 along the direction indicated by an arrow. The image of the work 1 is picked up by an imaging device 2 such as a CCD (Charge Coupled Device) camera, or the like, then converted into digital image data by an analog/digital converter (A/D) 3, and then input into a controller 4. In this case, assume that the work 1 is formed of a circular cylinder body in this embodiment.

The controller 4 is composed of a microprocessor as a main body of the inspection system of the present invention.

The controller 4 comprises a process executing section 41 for executing various processes by using a CPU, and a set process storing section 42 which consists of a nonvolatile storage medium such as a flash memory which functions as an inspection item storing means. The process executing section 41 is divided functionally into a data processor 411 which performs digital data processing of the image data, and an execution controller 412 which lets the data processor 411 execute the data processing and conducts control of the overall system.

The digital image data input from the A/D 3 to the controller 4 are subjected to the preprocessing (image correction such as exposure correction, relative position correction of the image of the work 1 in the visual field, and the like) by the data processor 411 and then stored in a memory 5. The memory 5 is formed of a normal RAM, and functions as an image data storing means which stores temporarily the image data. Such image data of the work 1 stored in the memory 5 are read by the data processor 411, then converted into analog image signals by a digital/analog converter (D/A) 7, and then displayed on a monitor 8.

Figures 2, 3:
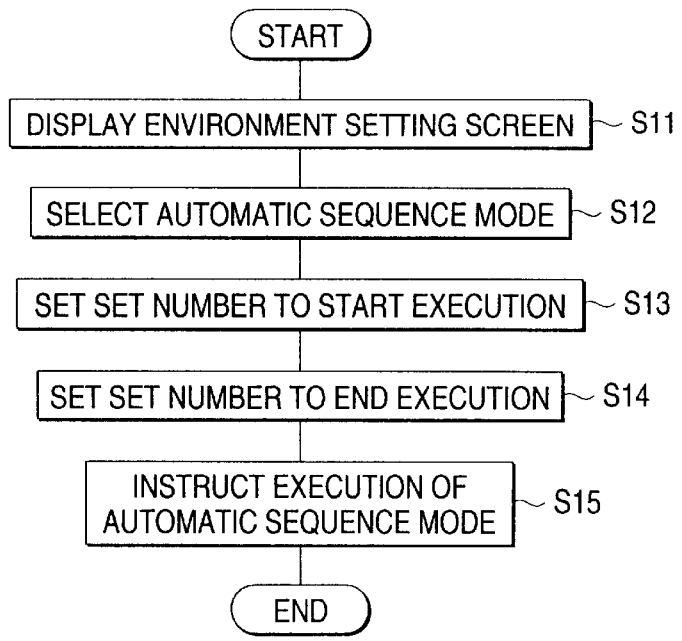
FIG. 2 is a schematic view showing contents set by a set process storing section in the inspection system according to the present invention.
FIG. 3 is a flowchart showing procedures of an operation of the inspection system according to the present invention.

The data processor 411 not only executes merely storing of the image data in the memory 5 and displaying of them on the monitor 8 as described above, but also functions as a data processing means which performs essential processes as the inspection system in compliance with the instruction issued from the execution controller 412. The processes to be performed by the data processor 411 are set previously in the set process storing section 42. FIG. 2 is a schematic view showing contents set in the set process storing section 42.

In the present embodiment, various data processes can be divided into groups from setting 1 to setting 16 and then set in the set process storing section 42. Eight inspection areas can be set in each setting group, and an inspection item can be registered in each inspection area. Such grouping is made mainly to set inspection contents contained in respective groups within the data processing capability of the data processor 411. Accordingly, if the data processing capability of the data processor 411 is large rather than that required for the inspection contents, the number of settings of the inspection contents contained in respective groups can be increased. Conversely, if the data processing capability of the data processor 411 is small rather than that required for the inspection contents, the number of settings of the inspection contents contained in respective groups must be reduced.

In an example shown in FIG. 2, processes for "an outer diameter, an inner diameter, an area", and the like are set previously in the setting 1 respectively, and processes for "a surface defect, an angle, a width dimension, an area", and the like are set previously in the setting 2 respectively. For example, as with the image detected by picking up an end surface of the circular cylinder work 1, the process for the "outer diameter" is a process which detects the concerned image of the work 1 in the image data on each main scanning line of the imaging device 2 to then decide whether or not a maximum value of the outer diameter is within a predetermined range. Also, the process for the "surface defect" is a process which decides whether or not either a shade of the image or difference in color exceeds a predetermined threshold value.

In this manner, the process executing section 41 must apply various processes, which correspond to respective processes stored in the set process storing section 42, to the digital image data of the work 1 stored in the memory 5. At that time, the image data which are picked up first once are employed, as they are, as the image data of the work 1 stored in the memory 5.

Reference numeral 10 denotes a control panel employed to control the inspection system manually. This control panel 10 functions as a designating means which sets various items containing the above process stored in the set process storing section 42 and controls start, stop, and the like of the inspection system. When the control panel 10 is to be employed, menus are displayed on a screen of the monitor 8.

Reference numeral 6 denotes an interface (I/O) employed to connect a personal computer 9 to the process executing section 41 of the controller 4. The I/O 6 functions as a designation receiving means when various items are set in the inspection system by the personal computer 9 or the inspection system is controlled by the personal computer 9, without the employment of the above control panel 10.

As evident from the above description, in accordance with the instruction issued from the I/O 6, which functions as the designation receiving means to receive the instruction supplied from the control panel 10 or the PC 9 which functions as the designating means, or the predetermined sequence, the execution controller 412, which functions as an executing means, reads process contents to be executed from the set process storing section 42, which functions as the inspection item storing means, and then causes the data processor 411, which functions as the data processing means, to execute the data processing.

Next, an operation of the above inspection system according to the present invention will be described with reference to a flowchart showing operational procedures hereinafter. In this case, in the following description, assume that the process contents are set previously in the setting 1 to the setting 8 of the set process storing section 42.

First, a mode used to execute the successive inspection by executing successively respective processes being set previously in the set process storing section 42 must be set. Processes taken for that purpose will be described with reference to a flowchart showing the procedures in FIG. 3 hereunder.

To begin with, when the control panel 10 is operated, the execution controller 412 of the controller 4 causes the monitor 8 to display an environment setting screen (step S11). The environment setting screen is a screen to set an operation mode of the inspection system. It is possible to select one of a mode in which only one type of inspection is conducted and a mode in which several types of inspection are conducted successively (automatic sequence mode) from the environment setting screen. Here the automatic sequence mode is selected (step S12).

Then, set numbers of the processes to be executed successively are input by operating the control panel 10. In the present embodiment, a head number and an end number of the processes to be executed successively are input (steps S13 and S14). In this case, it is needless to say that the set numbers may be input by designating individual set numbers arbitrarily. Such setting of the set numbers is stored in the memory 5. Finally, the execution controller 412 is instructed by operating the control panel 10 to start the operation in the automatic sequence mode (step S15).

Figure 4:
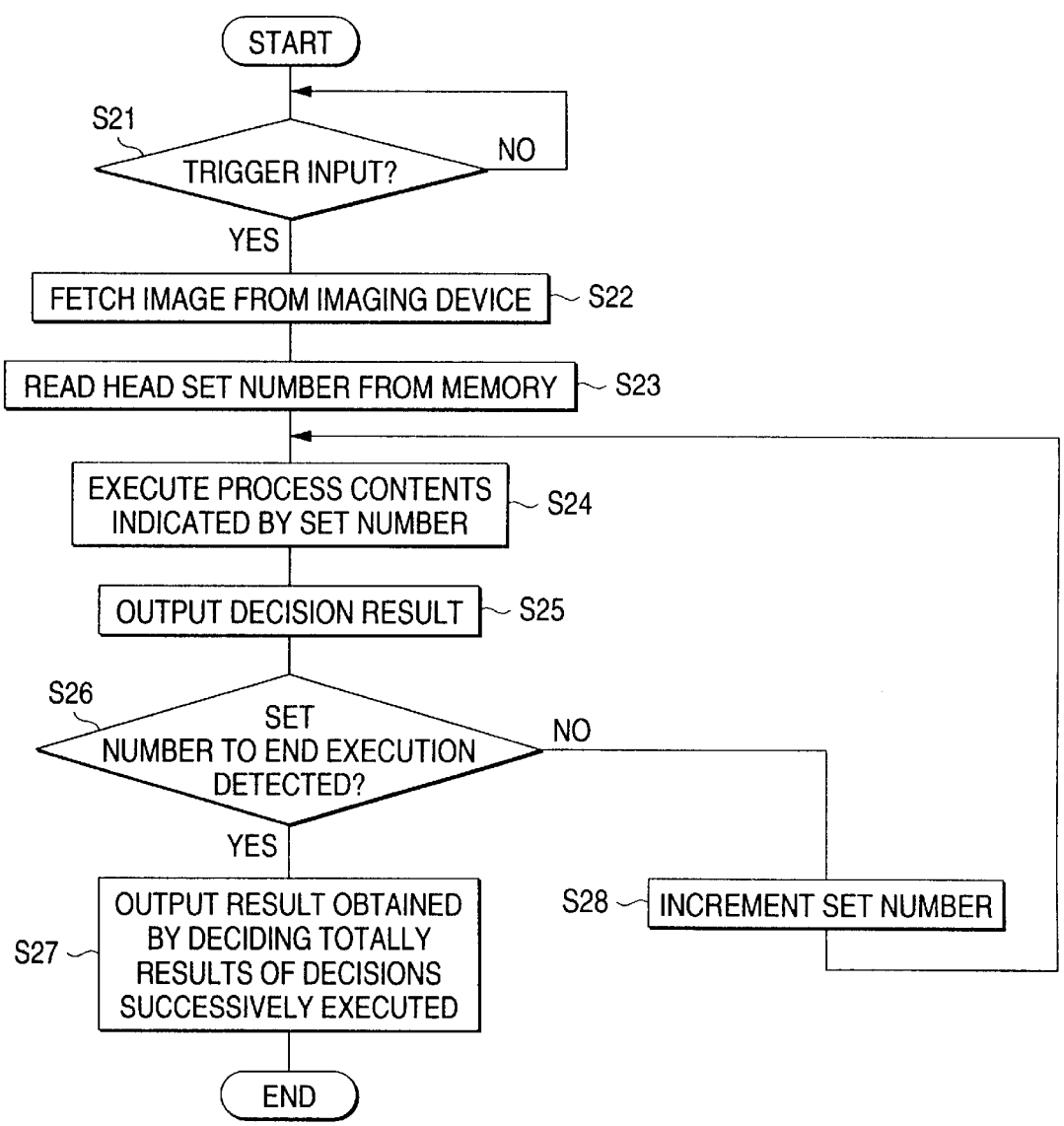
FIG. 4 is a flowchart showing procedures of another operation of the inspection system according to the present invention.

When the above settings are completed, the inspection system according to the present invention is operated as shown in a flowchart shown in FIG. 4. If a trigger instructing the start is input from the control panel 10 or the PC 9 (if "YES" in step S21), the execution controller 412 of the controller 4 renders the imaging device 2 to pick up the image of the work 1, then fetches digital image data from the imaging device 2, and then stores them in the memory 5 via the data processor 411 and also displays them on the monitor 8 (step S22). Then, the execution controller 412 reads the head set number of the process stored in the memory (step S23), then reads the process content indicated by the set number from the set process storing section 42, and then causes the data processor 411 to execute the process content indicated by the set number with respect to the digital image data of the work 1 stored in the memory 5 as a process object (step S24). This decision result is output to the monitor 8 or the PC 9 (step S25).

For example, as shown in FIG. 2, the processes for inspecting "the outer diameter, the inner diameter, the area", and the like are set previously as the setting 1 respectively, and the processes for inspecting "the surface defect, the angle, the width dimension, the area", and the like are set previously as the setting 2 respectively. Then, assume that these two set numbers are set as the inspections to be executed successively. In this case, the execution controller 412 reads the setting 1 which is the head set number stored in the memory 5, and then first executes the processes for "the outer diameter, the inner diameter, the area", and the like as the process contents in the setting 1. Then, the execution controller 412 decides whether or not the results are within a predetermined range.

Then, the execution controller 412 decides whether or not the set number of the process which is being executed currently by the data processor 411 coincides with the end set number stored in the memory 5 (step S26). If "NO" is step S26, i.e., unless all types of inspection to be executed successively have been completed yet, the set number is then incremented by "1" (step S28). Then, the process returns to step S24. In step S24, the process contents indicated by the succeeding set number are read from the set process storing section 42 to the execution controller 412, and then such process contents are executed by the data processor 411 relative to the digital image data of the work 1 stored in the memory 5 as the object.

As shown in FIG. 2, in case the processes for "the surface defect, the angle, the width dimension, the area", and the like are set in the setting 2 as the succeeding set number of the setting 1, the execution controller 412 reads the setting 2 as the succeeding set number stored in the memory 5 and then causes the data processor 411 to execute the succeeding processes for "the surface defect, the angle, the width dimension, the area", and the like as the process contents. Then, the results are output to the monitor 8 or the PC 9.

The execution controller 412 executes the above processes repeatedly in the same manner with respect to all set numbers up to the end set number stored in the memory 5. Finally, the execution controller 412 outputs the results, which are obtained by deciding totally the decision results detected by the processes indicated by respective set numbers, to the monitor 8 or the PC 9 (step S27).

During this operation, the execution controller 412 merely executes the process, which fetches the image data of the work 1 being picked up by the imaging device 2 from the imaging device 2, only once immediately after the trigger signal has been input in step S21. Therefore, the image of the work 1 is never fetched again from the imaging device 2 during when the processes indicated by respective set numbers are executed for plural types of inspection.

Figure 5:
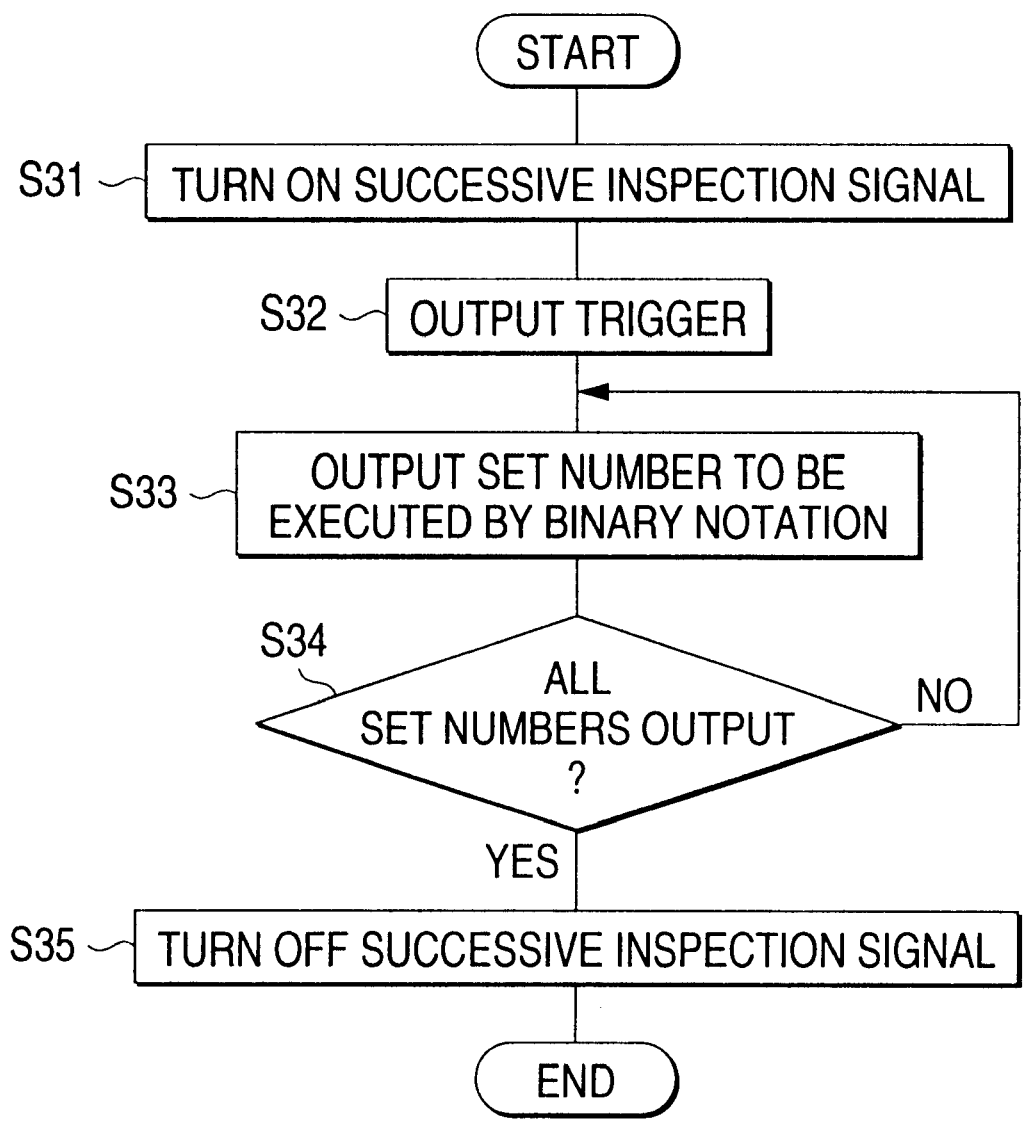
FIG. 5 is a flowchart showing procedures of still another operation of the inspection system according to the present invention.

The above operational procedures correspond to the case where inspection types of successive inspections are set by the control panel 10 and also the execution of successive inspections is instructed by the control panel 10. However, it is possible to set inspection types of successive inspections and also start the execution of successive inspections by instructing from the external PC 9 connected via the I/O 6. The operational procedures in such case will be described with reference to flowcharts shown in FIGS. 5 and 6 hereunder.

At first, the PC 9 outputs an ON signal of a successive inspection signal (step S31). The trigger signal for instructing the start of the inspection is then output (step S32). The set numbers of the inspection to be executed are then output as binary codes (steps S33 and S34). If it has been completed that all the set numbers of the inspection to be executed are output (if "YES" in step S34), the PC 9 outputs an OFF signal of a successive inspection signal (step S35). In this event, the above procedures may be programmed in advance in the PC 9, or else may be instructed to be executed every time by operating a keyboard or the like of the PC 9.

Figure 6:
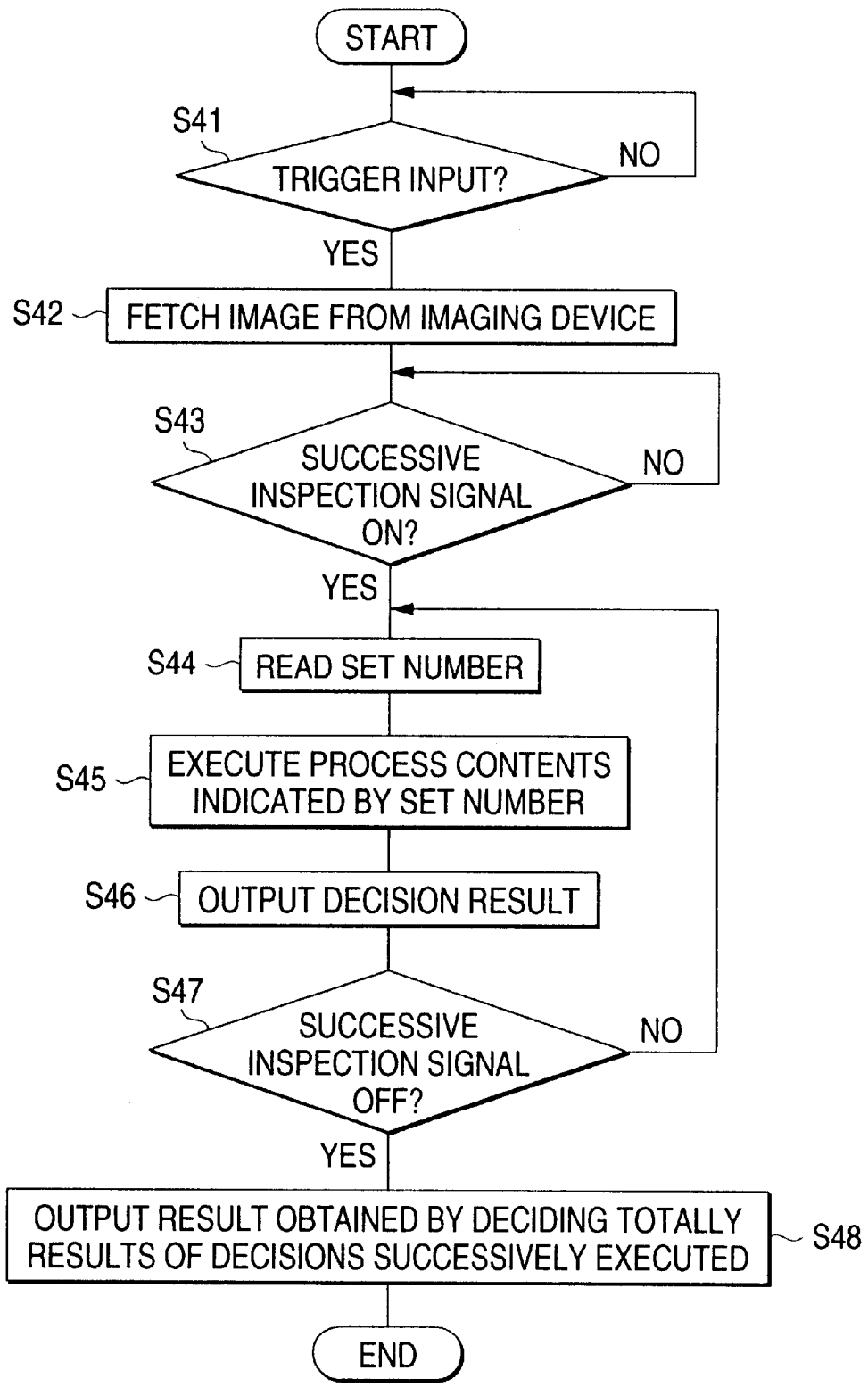
FIG. 6 is a flowchart showing procedures of still another operation of the inspection system according to the present invention.

Since the above signals being output from the PC 9 are input, the inspection system according to the present invention will be operated in accordance with the procedures shown in the flowchart of FIG. 6.

If the trigger signal being output from the PC 9 to instruct the start (step S32 in FIG. 5) is input (if "YES" in step S41), the execution controller 412 makes the imaging device 2 pick up the image of the work 1, then fetches the image from the imaging device 2, and then stores them in the memory 5 (step S42). In turn, if the ON signal of the successive inspection signal being output from the PC 9 in step S32 is input (if "YES" in step S43), the execution controller 412 reads the set number being output from the PC 9 (step S44). Then, the execution controller 412 reads the process contents indicated by the set number from the set process storing section 42, and then lets the data processor 411 execute the process contents indicated by the set number with respect to the digital image data of the work 1 stored in the memory 5 as the object (step S45). This decision result is output to the monitor 8 or the PC 9 (step S46).

Next, the execution controller 412 decides whether or not an ON output of the successive inspection signal supplied from the PC 9 is stopped (step S47). If the ON output of the successive inspection signal is still maintained (if "NO" in step S47), the process returns to step S44 where the set number being output from the PC 9 is read once again. That is, in step S44, the process contents indicated by the set number which is read newly from the PC 9 are read from the set process storing section 42 to the execution controller 412, and are executed by the data processor 411 with respect to the digital image data of the work 1 stored in the memory 5 as the object.

In the following, the processes are repeated similarly as above during when the ON output of the successive inspection signal supplied from the PC 9 is maintained. Conversely, if the successive inspection signal supplied from the PC 9 is changed into the OFF output (if "YES" in step S47), the execution controller 412 outputs the result obtained by deciding totally the decision results which are derived by the processes indicated by respective set numbers (step S48).

During this operation, the execution controller 412 merely executes the process, which fetches the image data of the work 1 being picked up by the imaging device 2 from the imaging device 2, only once immediately after the trigger signal has been input in step S41. Therefore, the image of the work 1 is never fetched again and again from the imaging device 2 during when the processes indicated by respective set numbers are executed for plural types of inspection.

In the above embodiment, it is possible to register eight types of set numbers in the set process storing section 42. However, the number of types of set numbers is specified by the data processing capability of the data processor 411. Therefore, there are cases where more registrations can be achieved according to the capability of the inspection system, or else there are cases where merely fewer registrations can be achieved conversely. However, a gist of the present invention resides in that various data processings with respect to the image data, which are picked up only once by the imaging process, can be executed sequentially in unit of group to thus conduct a variety of inspections.

As described above, according to the inspection system of the present invention, the image of the inspection object is picked up only once for the first time as the image data, and then the data processing is executed sequentially in unit of group which is formed by dividing the image data into a plurality of inspection items being assigned and stored previously. Therefore, such a necessity that the inspection object must be picked up for each data processing in respective groups which contain a plurality of inspection items can be eliminated, and a necessity of the mechanism for standing still the production line can also be eliminated.

According to the inspection system of the present invention, if several groups of previously stored groups are designated in advance, the data processing for the inspection items being contained in the groups can be executed sequentially in unit of group. Therefore, if the control panel, for example, is connected as the designating means, the processes of the group which is designated by the control panel can be sequentially and automatically executed.

Furthermore, according to the inspection system of the present invention, in case several groups of previously stored groups are designated in advance, such designation can be accepted and then the data processing for the inspection items being contained in the groups can be executed in unit of group. Therefore, if the interface to which the personal computer can be connected, for example, is provided as the designation receiving means, the data processing can be executed sequentially and automatically in unit of group by designating the groups in accordance with the programming of the personal computer.

What is claimed is:

1. An inspection system for conducting inspections of an object to be inspected by processing image data which are collected by picking up an image of the object to be inspected, comprising:

image data storing means for storing at least one set of the image data of the object;

data processing means for executing data processing of the image data stored in said image data storing means;

inspection item storing means having a plurality of setting groups, each of said setting groups being set a plurality of data processes as inspection items and the number of data processes set in each setting group being set within data processing capabilities of said data processing means;

designating means for designating one setting group or plural setting groups to cause said data processing means to execute data processing sequentially corresponding to said only once picked-up image of the object; and executing means for causing said data processing means to execute data processing based on said data processes of said one setting group or said plural setting groups designated by said designating means.

2. The inspection system according to claim 1, further comprising designation receiving means for receiving designation of at least one group out of the plurality of said setting groups stored in said inspection item storing means, wherein said executing means is constructed to cause said data processing means to sequentially execute the data processing in units of groups received by said designation receiving means.

3. The inspection system according to claim 1, wherein the executing means is configured to include at least one operation mode, each of said at least one operation mode includes at least one inspection item, and said executing means is further configured to allow selection of the at least one operation mode such that, depending on the operation mode selected, one of a single inspection item and a plurality of related inspection items associated with the at least one operation mode is data processed.

4. The inspection system according to claim 1, wherein each of said setting groups of said inspection item storing means can be set inspection area to execute data processes set in the same setting group.

5. The inspection system according to claim 1, wherein said designating means designates said one setting group when the whole data processes corresponding to the image of the object to be inspected are set in said specified setting group, and wherein said designates said plural setting groups to executing data processes of the setting groups sequentially, when the whole data processes corresponding to the image of the object to be inspected are set in said specified plural setting group separately.

6. The inspection system according to claim 5, wherein said designating means determines a turn of said setting group to carry out the data processes set in said setting group.

7. The inspection system according to claim 1, wherein said data processes set in said setting group include a data process to detect at least one of diameter area and angle of the image of the object to be inspected.

8. The inspection system according to claim 7, wherein said data processes set in said setting group include a data process to detect diameter area and angle of the image of the object to be inspected.

* * * * *